United States Patent [19]

Shie et al.

[11] Patent Number: 5,659,127

[45] Date of Patent: Aug. 19, 1997

[54] SUBSTRATE STRUCTURE OF MONOLITHIC GAS SENSOR

[75] Inventors: Jin-Shown Shie, Hsinchu; Hsin-Fang Lei, Chung-Li, both of Taiwan

[73] Assignee: OPTO Tech Corporation, Taipei, Taiwan

[21] Appl. No.: 701,799

[22] Filed: Aug. 26, 1996

[51] Int. Cl.$^6$ .................................................. G01N 27/12
[52] U.S. Cl. .................... 73/31.05; 73/335.05; 422/88; 422/94; 338/334
[58] Field of Search ....................... 73/31.05, 31.06, 73/335.05; 422/90, 94, 88; 338/34

[56] References Cited

U.S. PATENT DOCUMENTS

| | | | |
|---|---|---|---|
| 4,198,850 | 4/1980 | Firth et al. | 73/23 |
| 4,198,851 | 4/1980 | Janata | 73/23 |
| 4,224,280 | 9/1980 | Takahama et al. | 422/98 |
| 4,343,768 | 8/1982 | Kimura | 422/97 |
| 4,345,985 | 8/1982 | Tohda et al. | 204/192 EC |
| 4,358,951 | 11/1982 | Chang | 73/23 |
| 4,481,499 | 11/1984 | Arima et al. | 338/34 |
| 4,580,439 | 4/1986 | Manaka | 73/23 |
| 4,596,975 | 6/1986 | Reddy et al. | 338/34 |
| 4,656,863 | 4/1987 | Takami et al. | 73/23 |
| 4,706,493 | 11/1987 | Chang et al. | 73/23 |
| 4,792,433 | 12/1988 | Katsura et al. | 422/98 |
| 4,885,929 | 12/1989 | Kasahara et al. | 73/23 |
| 4,928,513 | 5/1990 | Sugihara et al. | 73/1 G |
| 5,012,671 | 5/1991 | Yagawara et al. | 73/31.06 |
| 5,013,396 | 5/1991 | Wise et al. | 156/628 |
| 5,159,413 | 10/1992 | Calviello et al. | 505/1 |
| 5,293,041 | 3/1994 | Kruse, Jr. et al. | 250/338.3 |
| 5,367,283 | 11/1994 | Lauf et al. | 338/34 |
| 5,447,054 | 9/1995 | Modica et al. | 73/31.06 |

OTHER PUBLICATIONS

Catalogue of a product with Model No. TGS813 of Figaro Engineering, Inc., Whole catalogue.
Wee-Hin et al, "Motorola Micromachined Thin-Film Gas Sensor", Technical data from Sensors Expo. 1996 Exhibition in Anaheim Los Angeles.

*Primary Examiner*—Hezron E. Williams
*Assistant Examiner*—J. David Wiggins
*Attorney, Agent, or Firm*—Cushman Darby & Cushman IP Group of Pillsbury Madison & Sutro LLP

[57] ABSTRACT

A substrate structure of a monolithic gas sensor is disclosed, wherein the substrate structure is formed as a thermal resistant and insulating suspended thin plate configuration on a single crystal silicon substrate. The thin plate has formed thereon a heating resistor and coated with tin-oxide-base reducing gas-sensitive material. The thermal resistant thin plate formed on the silicon substrate comprises a native silicon oxide layer, a silicon-rich silicon nitride layer deposited on the native silicon oxide layer, and a top silicon oxide layer formed by thermal oxidation of a surface layer of the deposited silicon-rich silicon nitride layer. An oxide-nitride-oxide sandwiched composited configuration is thus formed that can relieve mechanical stresses internal to the thin plate. The suspended thermal resistantthin plate has corrugation portions formed near the plate edges for relieving mechanical stresses arising from thermal expansion of the silicon substrate and the thin plate when heated to high temperature. The heating resistor formed on the thin plate comprises a polysilicon layer and is covered by a passivation and then by an aluminum oxide layer having a thickness of about several hundred angstroms. The coated tin-oxide-based material is formed by thick-film screen printing to form a sensor film for the single-chip sensing element. Improved thermal and mechanical stress characteristics are obtained while achieving lower electrical power consumption and also maintaining low cost of manufacturing when batched produced.

5 Claims, 11 Drawing Sheets

SUBSTRATE STRUCTURE OF MONOLITHIC GAS SENSOR

BACKGROUND OF THE INVENTION

1. Field of the Invention

The present invention relates in general to the substrate structure of a monolithic gas sensor. In particular, the invention relates to the substrate structure better thermal stress characteristics that can be fabricated in simple semiconductor fabrication procedural steps.

2. Technical Background

Micromachining techniques have been advancing at a rapid rate for the last several decades, especially in the category of devices employing single crystal silicon for substrate material. One of the major applications of such techniques is in the fabrication of microsensors. Fabrication techniques of these microsensors are very similar to that for microelectronic devices. Batch manufacturing of these microsensors are widely employed, with relatively much lower costs than for the production of many conventional single-element sensing elements.

One important application of these sensing elements is the use as sensors for the existence of poisonous gases. Specific material (or materials) reacts with certain gases hazardous to human health, in order to signify the existence of such gases. Based on such detected reactions, the presence of such hazardous gases may also be expressed in quantity. There are quite many such sensing elements, such as those disclosed in U.S. Pat. Nos. 4,198,950; 4,224,280;and 4,792,433 for carbon monoxide. Among them, those employing tin oxide as sensor material and implemented as sensing elements which can be seen in markets are shown in FIGS. 5, 6 and 7.

Figure 5A:
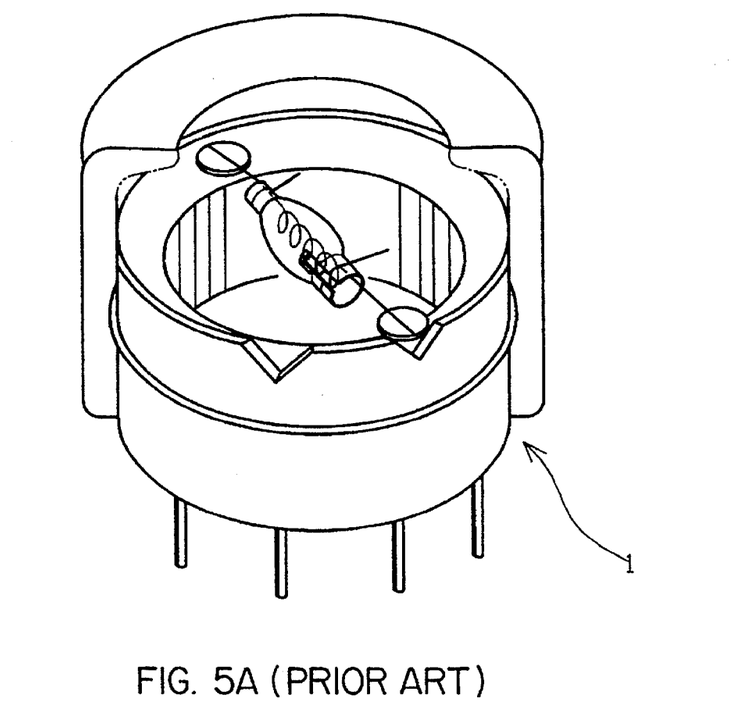
FIG. 5 shows the partially cut-away perspective view of a conventional gas sensing element with an enlarged detail of the ceramic tube gas sensor used therein.
Figure 5B:
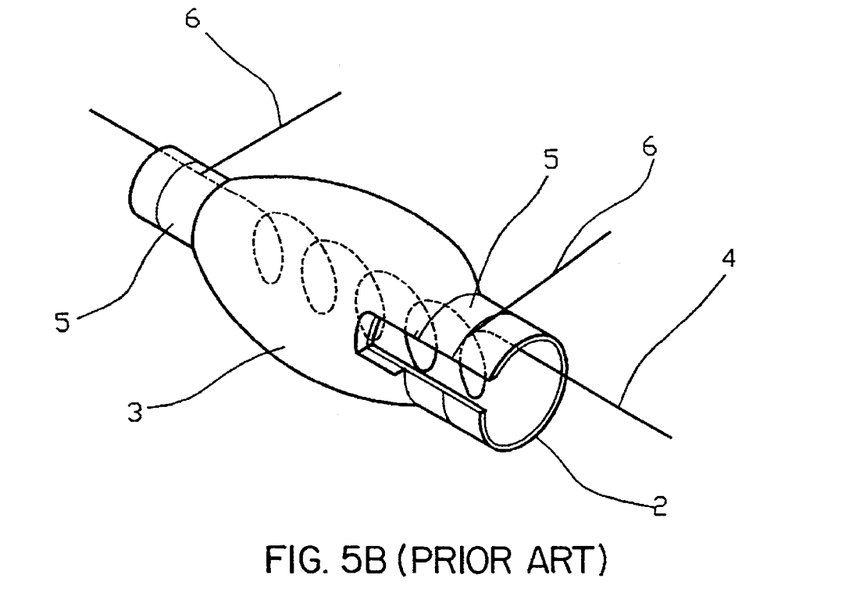

The sensing element depicted in FIG. 5 is one that was developed earlier although still in use currently. The sensing element is shown in the drawing to be comprised of device base 1, ceramic tube 2, tin oxide film 3 coated over the surface of ceramic tube 2, heating resistor coil 4, electrode 5 and lead wires 6. All those portions seen in the drawing other than the device base 1 comprises the sensing element body. The ceramic tube 2 is heated to a temperature of about 300° to 400° C. when the sensing element is used. At this temperature, the specially fabricated tin oxide film 3 is particularly sensitive so that it would be reacting with certain reducing gases. When such reactions take place, electrical resistance in the film would change (decrease under normal circumstances). Lead wires 6 provided at both ends of the device may therefore be connected to an external circuitry for conducting measurements on the extent of resistance change. This allows for the quantification, in addition to the detection, of those gases suspected to be present.

In the structural configuration schematically depicted in FIG. 5, physical size of the sensing element is relatively bulky. Further, due to the fact that ceramic tube 2 and heating coil 4 are widely separated apart from each other, considerable electrical power therefore has to be consumed before the temperature can be heated up to several hundred degrees Celsius. In addition, sensing element heated to high temperature must be separated from the supporting base 1 utilizing suspension means such as inactive platinum strings having high melting temperature. This substantially avoids direct physical contact between body of the sensing element and the supporting device base 1, so that thermal leakage from heated sensor body to a base 1 can be prevented. Since this type of gas sensors have a structure that is manufactured as discrete units, specially-designed automated manufacturing facilities must be used for production, costs are therefore high.

Figure 6A:
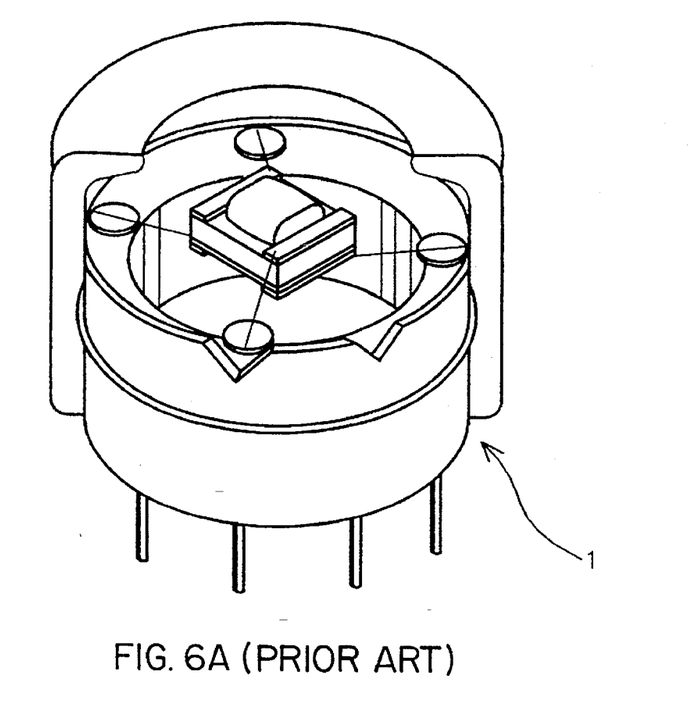
FIG. 6 shows the partially cut-away perspective view of a conventional gas sensing element with an enlarged detail of the thick film gas sensor used therein.
Figure 6B:
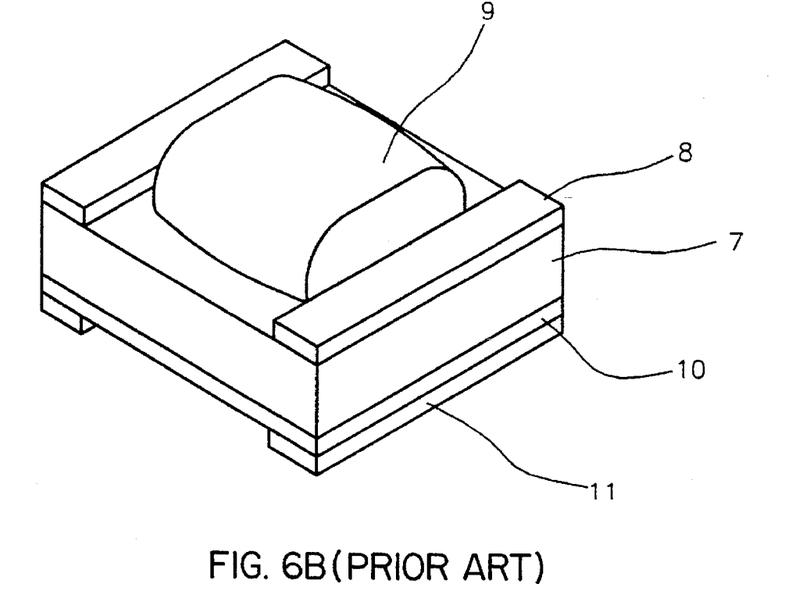
Figure 7:
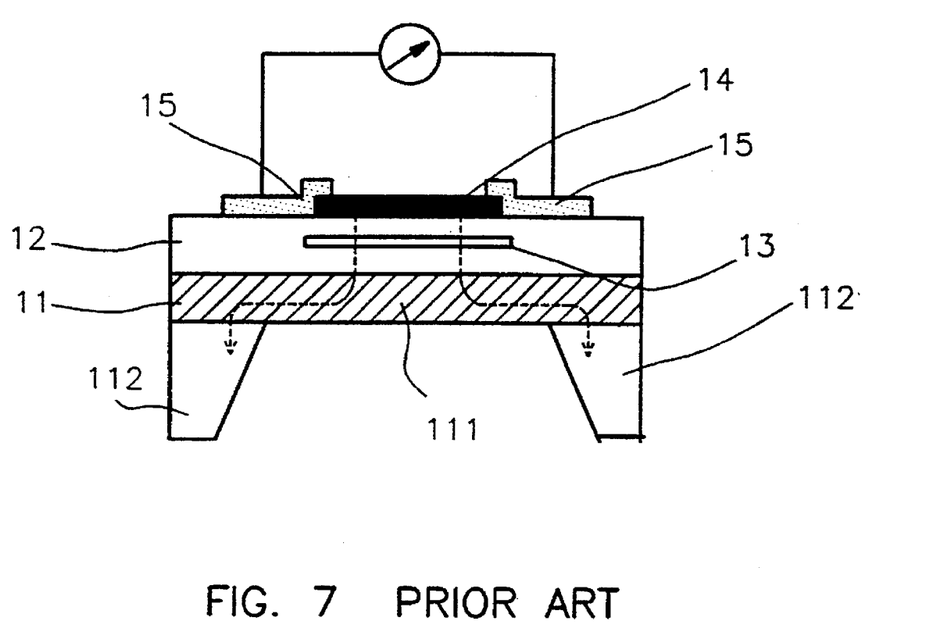
FIG. 7 schematically shows the cross-sectional view of the conventional monolithic gas sensor.

FIG. 6 shows the partially cut-away perspective view of a conventional gas sensing element developed in recent years. The sensing element is shown in the drawing with an enlarged detail of the thick film gas sensor used therein. As can be seen, the sensing element is also comprised of a sensing element body and the device supporting base 1. Essentially, the sensing element body consists of an aluminum oxide ceramic base 7, heating resistor 10, gold-plated electrodes 8 and the tin oxide sensor layer 9. Heating resistor 10 may be made, for example, of $RuO_2$ thick-film resistor. This sensor structure employs aluminum oxide ceramic as the base material that replaces the ceramic tube in the element of FIG. 5. Thick film screen printing technique is utilized to manufacture the heating resistor 10, sensor layer material 9 and electrodes 8 at both sides of the sensing element body. Similar structures had been disclosed in quite many U.S. patents, such as U.S. Pat. Nos. 4,792,433; 4,345,985; 4,224,280; 4,885,929 and 4,198,850. Although such sensing element body can be batch produced based on thick film processing technology, however, suspension structure is still required when the sensing element body is to be sealed in the device carrier. This is for the same reason of thermal isolation between the sensor body and the device base 1. Different kinds of supporting structures for good thermal isolation have been patented, such as those disclosed in U.S. Pat. Nos. 4,596,975 and 4,656,863. However, in these disclosures sealing remains to be the high cost portion for the manufacture of these single-unit sensing elements. Moreover, substrate surface area of these sensing elements remains to be relatively large as the screen printing technique has limited precision capability which contributes directly to the excessive amount of gas conductive heat loss in the surrounding atmosphere. Typical thermal power consumption is in the range of several hundred milli-watts. For a sensor system operating on battery power, this power consumption rating is barely practical.

Gas sensing elements based on micromachining fabrication technology have recently been patented and/or commercialized. An example is the device structure depicted in FIG. 7 as manufactured by Motorola in U.S. Pat. No. 4,706,493 by Chang et al. The cross-sectional view schematically depicted in the drawing shows that the device is fabricated utilizing a single crystal silicon substrate 11 as basis. A silicon nitride or oxide layer 12 is formed on the surface of the substrate 11 as an insulating layer, with the heating resistor 13 for the device embedded therein. A tin oxide sensor layer 14 is formed on the surface of the insulating layer 12 which is connected to external circuitry via a pair of contact electrodes 15. This is a structural configuration employing anisotropic back-side etching technique to form the thin insulating layer 12 substantially suspended above the surface of (100) silicon single crystal substrate 11. On top of the thin layer 12, heating resistor 13 and sensor film 14 may be formed by photolithographic technique.

In this depicted Motorola configuration, a heavily-boron-doped epitaxial silicon region 111 is formed in the substrate 11 underneath the thin insulating layer 12. Existence of this region serves to suppress the etching consumption to the region having a boron concentration of about $10^{19}$–$10^{20}/cm^3$. This allows for formation of the layer with predetermined thickness (i.e., the heavily-boron-doped epitaxial silicon layer 111). On the other hand, since a sensing element is subject to great structural distortion under high temperature as a result of excessive thermal stress. However, since boron-doped epitaxial silicon layer 111 has a thermal expansion coefficient substantially the same as that of the other portions of the silicon substrate 11, therefore, damage to the overall substrate structure can be prevented by sharing to withstand the stress produced internal to the insulating layer 12.

Figure 8:
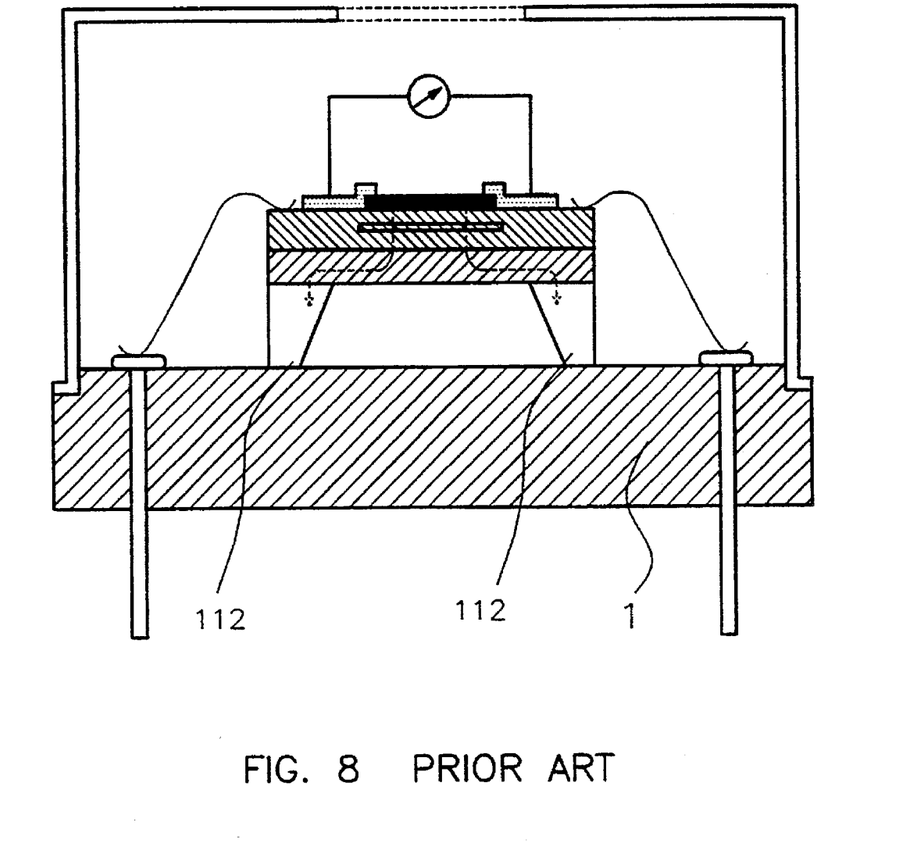
FIG. 8 shows the cross-sectional view of the monolithic gas sensor of FIG. 7 as it is sealed in a device carrier.

Sensor element shown in FIG. 7 has an overall structural surface area of about several tens of square milli-meters. Joule heat leakage to the supporting base 1 seen in FIG. 8 as produced by the thin layer 12 that amounts to solid conductive loss is generally transferred along the direction as schematically expressed in FIG. 7 by phantom arrow-headed paths. The heat is transferred from the thin layer 12 to the un-etched silicon substrate supporting pads 112. Since silicon is a good heat conductor, silicon substrate supporting pads 112 may therefore have low thermal resistance characteristics. As a result, the temperature difference between the high-temperature sensor layer 14 and the room temperature supporting base falls on the thin layer 12. The silicon supporting pads 112 may thus be stabilized at the temperature close to that of the supporting base. The monolithic gas sensor can therefore be directly bonded to the supporting base having good thermal conductivity characteristics without increased thermal loss, and the supporting base may be kept at relatively normal temperature. Sealing for this type of sensing element does not require the conventional suspension mechanism (such as those employed for the sensing elements depicted in FIGS. 5 and 6) in order to isolate hear transfer. Instead, TO metal-can packaging for conventional microelectronic circuit devices can be used in a simple and easy manner. The cross-sectional view of FIG. 8 depicts an example of this type of packaging. Since standardized packaging material and automated packaging equipments are readily available, costs can therefore be greatly reduced. Meanwhile, traditional suspension packaging mechanisms described above employing fine and long platinum strings for soldered suspension would require lower lead wire thermal loss and higher mechanical strength characteristics. In comparison, monolithic gas sensors fabricated out of micromachining technique have lead wires thereof placed and soldered to the top of the silicon supporting pads. This top portion of the silicon supporting pads has a temperature close to that of the silicon pad, there is therefore no concern of thermal loss via the conduction of the soldered lead wires. In addition, weight of the sensor chip is supported directly by the entire support base 1, the problem of mechanical strength of the wires is practically non-existent. As a result, standard and cheap gold bonding wires may be used for electrical connection. In other words, utilizing gold bonding wires in standardized and automated bonding operation of the sensing elements would incur much less manual intervention as well as much lower costs than when platinum strings are used.

Gas sensing elements implemented in the form as single-chip units may thus enjoy many advantages than their traditional counterparts. In summary, these advantages may be compared in the following Table 1.

TABLE 1

| | Ceramic Tube | Thick Film | Single-chip |
|---|---|---|---|
| Packaging | | | |
| Structure | ●Suspended | Suspended | Placed and |
| Production | ●Single-unit | Single-unit | bonded |

TABLE 1-continued

| | Ceramic Tube | Thick Film | Single-chip |
|---|---|---|---|
| | production | production | Batch production, |
| | ●Difficult to automate | Difficult to automate | Standardized and automated fast |
| | Slow Production | Slow production | production |
| Material | ●Platinum suspension wire, expensive | Platinum suspension wire, expensive | Gold bonding wires, low cost |
| | ●Non-standard supporting base | Non-standard supporting base | Standard TO-can supporting base |
| | ●Requiring special custom design | Requiring special custom design | Easy to acquire and low in cost |
| Sensor Element | | | |
| Size | Large | Medium | Small |
| Current consumption | Large (About 1A) | Medium (about 200 mA) | Small (50 mA or smaller) |
| Fabrication process | Single-unit production (Slow) | Thick-film batch production (Fast) | Micromachining batch production (Fast) |
| Precision | Low | Medium | High |
| Cost | High | Medium | Low |
| Battery operation | Not practical | Difficult | feasible |
| Circuitry integration | Not Possible | Not Possible | feasible |

From the comparisons outlined in Table 1 above, the monolithic gas sensor of FIG. 7, although superior than the conventional ones by at least the listed advantages, still suffers the following drawbacks. Specifically, with reference to FIG. 8, since silicon is a material of good thermal conduction, with a thermal conduction coefficient about 120 times that of silicon oxide, and about several tens of times that of silicon nitride, therefore, heat in high temperature region of the thin insulating layer 12 can be transferred to the supporting base 1 in a fast rate via the heavily-doped epitaxial silicon layer 111 directly underneath the layer 12. Thus, the problem of thermal power loss in such sensing elements is still unsolved.

SUMMARY OF THE INVENTION

It is therefore an object of the present invention to provide a substrate structure for monolithic gas sensors having reduced electrical-thermal power loss.

It is another object of the present invention to provide a substrate structure for monolithic gas sensors having reduced power consumption while simultaneously maintains good thermal stress characteristics.

The present invention achieves the above-identified objects by providing a substrate structure of monolithic gas sensor, wherein the substrate structure is formed as a thermal resistant and insulating suspended thin plate configuration on a single crystal silicon substrate. The thin plate has formed thereon a heating resistor and coated with tin-oxide-based reducing gas-sensitive material. The thermal resistant thin plate formed on the silicon substrate comprises a native silicon oxide layer, a silicon-rich silicon nitride layer deposited on the native silicon oxide layer, and a top silicon oxide layer formed by thermal oxidation of a surface layer of the deposited silicon-rich silicon nitride layer. An oxide-nitride-oxide sandwiched composite configuration is thus formed that can relieve mechanical stresses internal to the thin plate. The suspended thermal resistant thin plate has corrugation portions formed near the plate edges for relieving mechanical stresses arising from thermal expansion of the silicon substrate and the thin plate when heated to high temperature. The heating resistor formed on the thin plate comprises a polysilicon layer and is covered by a passivation and then by an aluminum oxide layer having a thickness of about several hundred angstroms. The coated tin-oxide-based material is formed by thick-film screen printing to form a sensor film for the single-chip sensing element.

BRIEF DESCRIPTION OF THE DRAWING

Other objects, features, and advantages of the present invention will become apparent by way of the following detailed description of the preferred but non-limiting embodiments. The description is made with reference to the accompanied drawings in which.

DETAILED DESCRIPTION OF THE PREFERRED EMBODIMENT

Figure 1:
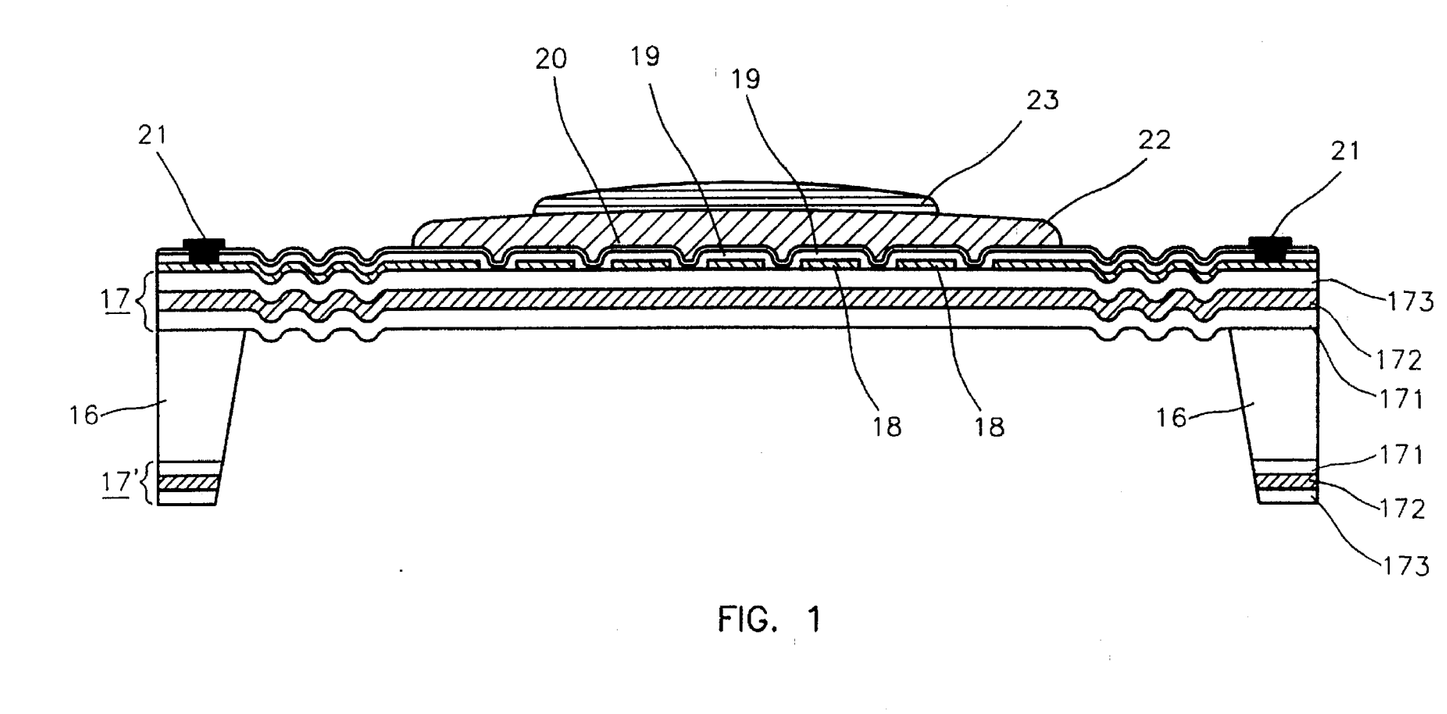
FIG. 1 schematically shows the cross-sectional view of the substrate of the monolithic gas sensor fabricated in accordance with the preferred embodiment of the invention.

Refer to FIG. 1 of the drawing. FIG. 1 schematically shows the cross-sectional view of the substrate of a monolithic gas sensor fabricated in accordance with a preferred embodiment of the invention. The inventive substrate structure for monolithic gas sensors includes primarily a silicon substrate 16, as well as sandwiched composite structures 17 and 17' formed on top and beneath the substrate 16 respectively. Each of the upper and lower composite structures 17 and 17' is made up of three constituent layers. These include a native oxide layer 171 of silicon formed in a thermal oxidation procedure, a silicon-rich silicon nitride layer 172, and a silicon oxide layer 173 formed by thermal oxidation of silicon nitride. Among the two, composite structure 17 has formed therein a pair of corrugated portions seen in the cross-sectional view near the ends. These structural corrugations serve to relieve mechanical stresses generated internal to the substrate structure as device is being heated for operation. A multiple of heating resistor sections 18 are seen formed on the surface of the composite structure 17. Note that the cross-sectional view reveals the multiple sections of the single heating transistor as cut through along the observing plane. Over the surface of these heating resistor sections 18, passivation layers 19 are formed, followed by the formation of an aluminum oxide layer 20 having a thickness of at least about several hundred angstroms. Gold platings 21 are then formed as the electrodes on the surface of the aluminum oxide layer 20 each at the extreme ends of the substrate as seen in the drawing. A layer of tin-oxide-based material 22 is then formed over the surface of the aluminum oxide layer 20 coveting a large center area thereof and used as the sensor layer. A catalyst layer 23 further covers the surface of the sensor layer 22.

Formation of the sandwiched composite structure 17 may be implemented in the process as described below. First of all, the native silicon oxide layer 171 is formed by thermal oxidation. Deposition of silicon nitride layer having high silicon content follows to form the silicon-rich silicon nitride layer 172. Finally, surface of the silicon-rich silicon nitride layer 172 is oxidized to form the silicon oxide layer 173. An oxide-nitride-oxide composition is thus established.

As mentioned above, the sandwiched composite structure 17 having corrugation regions formed therein has the capability to relieve to the mechanical stresses arising internal to the composition as a result of heat build-up. The stress-relief capability of this composite structure is based on the following reasons. First of all, thermal coefficient of expansion for silicon is larger than that for silicon oxide but is smaller than silicon nitride. Therefore, under proper fabrication procedural conditions as well as proper geometrical arrangement, it is possible that the compressive stress arising internal to the silicon oxide layer may annihilate partially, or even completely, the tensile stress arising internal to the silicon nitride layer. Secondly, presence of these corrugation regions can assist in the relief of stress generated as a result of thermal expansion between the thin layer and the silicon substrate 16 when the entire substrate structure is heated to high temperature.

Presence of the composition structure 17' at the bottom side of the substrate does not have any specific effect. This composition structure 17' is formed automatically when the composite structure 17 is fabricated as described above. However, when the back-side etching procedure is implemented, this composition structure 17' may be used as the etching mask.

On the surface of the sandwiched composite structure 17, heating resistor sections 18 must be formed, as is described above. Special tin-oxide-based material that is reactive with respect to reducing gases must then be coated further on. A substantial procedural is as follows. First heating resistor elements 18 are formed over the surface of the oxide layer 173. Passivation 19 is then formed to cover the resistor sections 18. Then an aluminum oxide layer 20 is further formed on top of the passivation layer 19 having a thickness of about several hundred angstroms. After the aluminum oxide layer 20 is formed, surface thereof is then coated with a tin-oxide-based sensor layer 22. There are at least two reasons to require the presence of the aluminum oxide layer 20. First, top surface of the sensing element of the invention may thus exhibit the same physical and chemical characteristics as that of the aluminum oxide base of the conventional sensing elements. Conventional thick-fill technique (the sensing element body depicted in FIG. 6) may therefore be applied to the sensing element of the invention. Next, presence of the aluminum oxide layer 20 is suitable for preventing the direct contact between the silicon oxide and the tin oxide. Since silicon and tin are elements of the same group, un-predictable results may be achieved if both are treated under high temperature. Physical isolation between the two is therefore necessary.

Such aluminum oxide layer 20 may be formed via any of the following two methods. First, aluminum oxide may be directly coated in a physical vapor deposition procedure, an electron beam deposition, or a high frequency sputtering. Secondly, aluminum oxide may be deposited in advance and then subject to oxidation in a water vapor environment heated to about 450° C., or it may be formed in a low temperature anode oxidation procedure.

In a preferred embodiment of the substrate structure of the invention, heating resistor sections 18 may be formed of polysilicon. In this case, surface of the polysilicon may be directly oxidized to form passivation layer 19.

In another preferred embodiment, heating resistor sections 18 may be formed of platinum. In this case, chemical vapor deposition procedure may be used to deposit a layer of oxide or nitride to form the passivation layer 19.

In a preferred embodiment, the tin-oxide-based sensor material 22 may be formed in a spin coating procedure, or it may be formed by thick fill screen printing.

Figure 2:
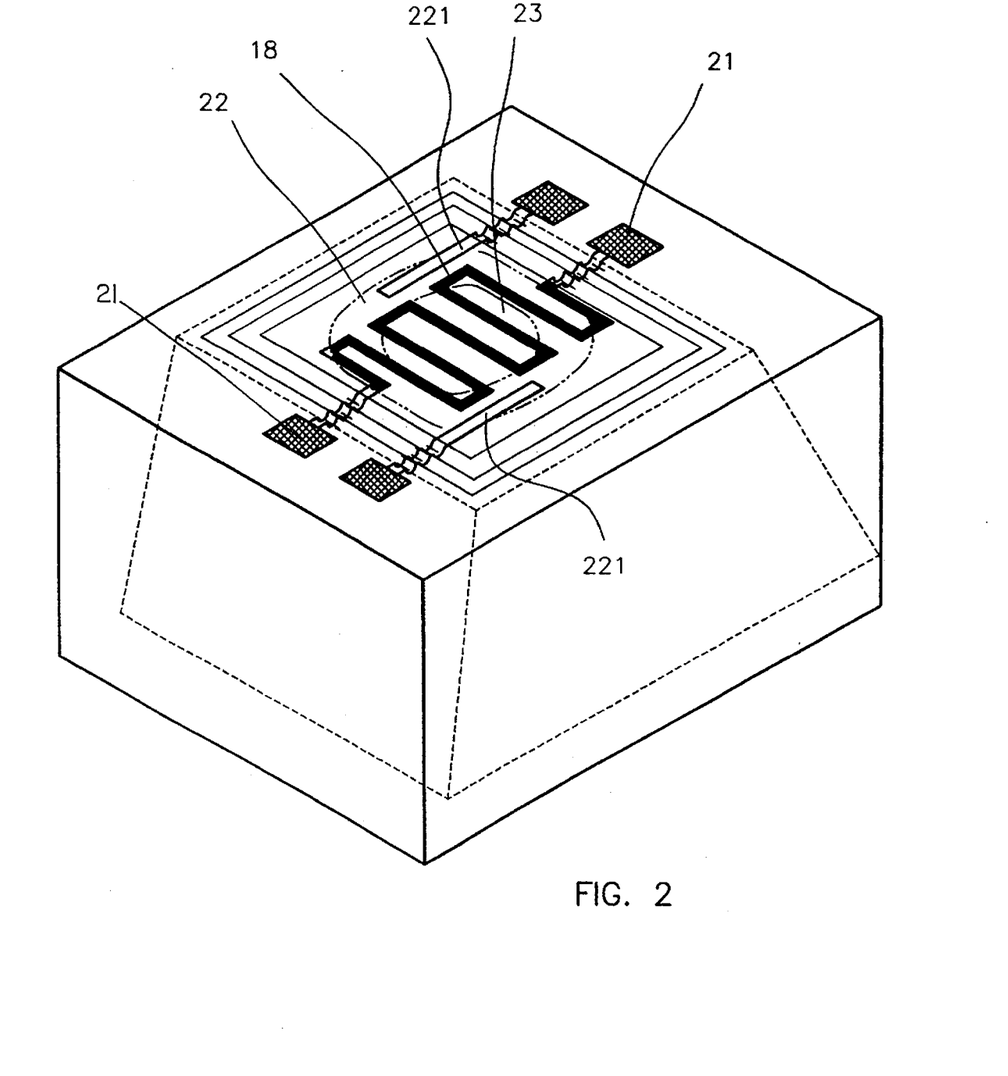
FIG. 2 is a perspective view showing substrate structural configuration of the monolithic gas sensor fabricated in accordance with the preferred embodiment of the invention.

FIG. 2 is a perspective view showing substrate structural configuration of the monolithic gas sensor fabricated in accordance with the preferred embodiment of the invention. The trapezoidal cube indicated by the phantom line inside the entire block is the portion of the substrate to be removed in a back-side etching procedure. As is seen in the drawing, the substrate structure includes the heating resistor 18, electrodes 21, tin-oxide-based sensor fill 22, sensor electrodes 221 and catalyst layer 23. Electrode 221 for the tin-oxide-based sensor film 22 are not explicitly shown in the cross-sectional view of FIG. 1. This is because the cutting plane for revealing the cross-sectional structure does not cross over any of the two sensor electrodes, but rather, crosses over the two electrodes 21. The sensor electrodes 221 may be used to measure the resistance in the tin-oxide-based sensor film 22 by connection to external electric circuitry not shown in the drawing.

Figure 3A:
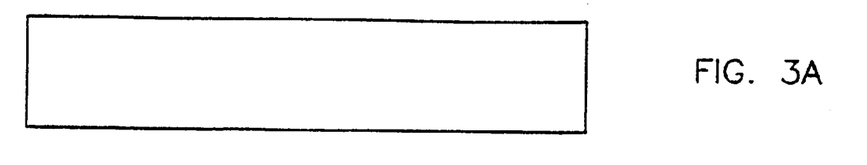
FIGS. 3A–3R are cross-sectional views of the substrate of the monolithic gas sensor fabricated in accordance with the preferred embodiment of the invention as depicted in the selected process stages.
Figure 3B:
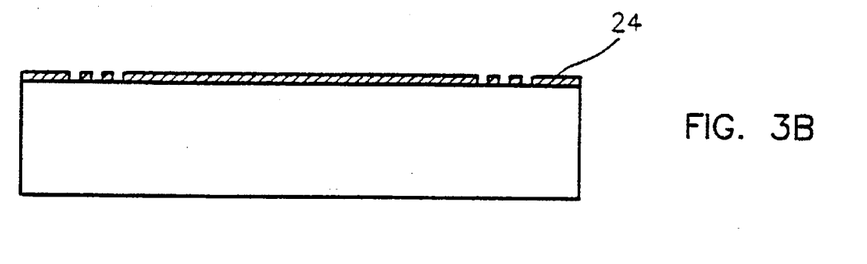
Figure 3C:
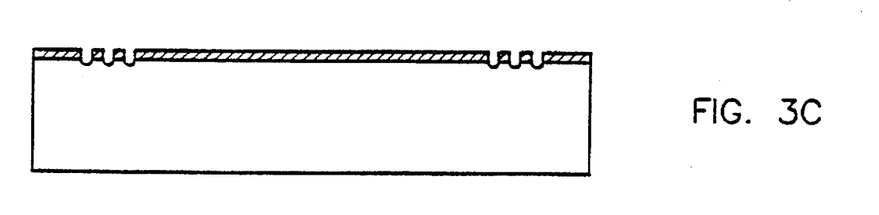
Figure 3D:
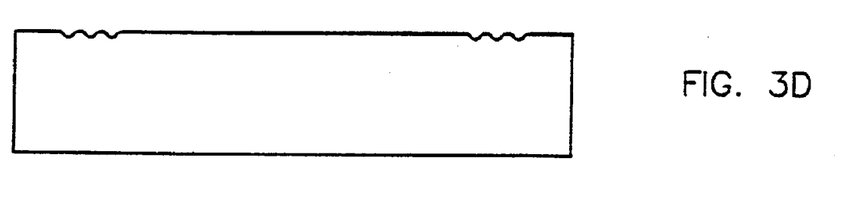
Figure 3E:
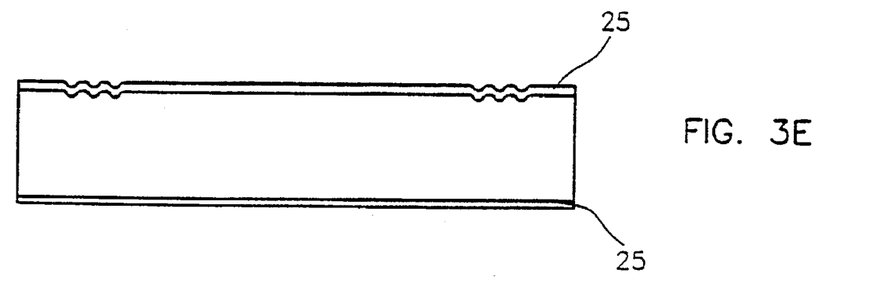
Figure 3F:
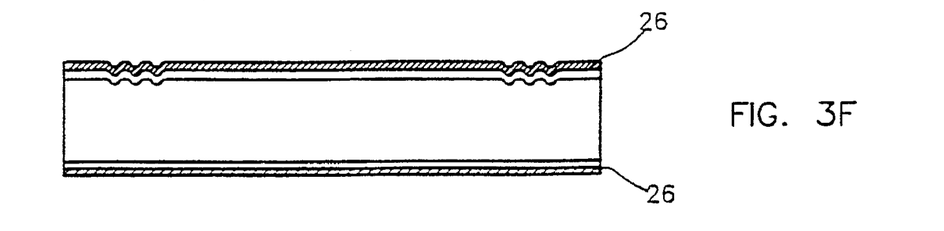
Figure 3G:
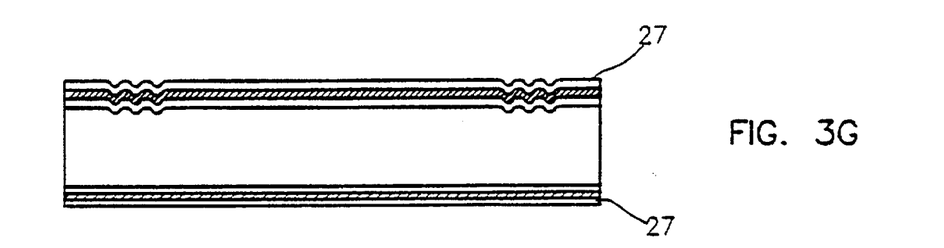
Figure 3H:
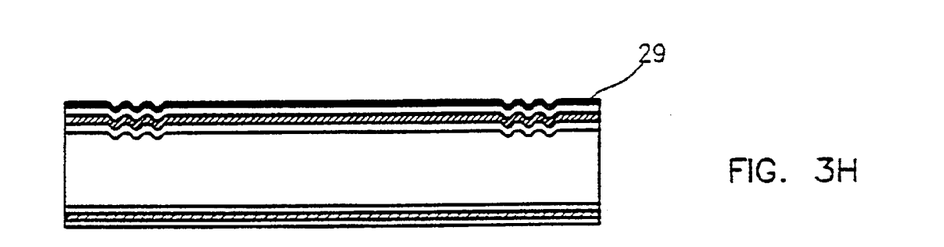
Figure 3I:
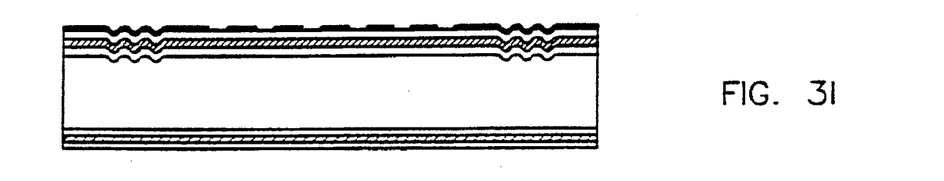
Figure 3J:
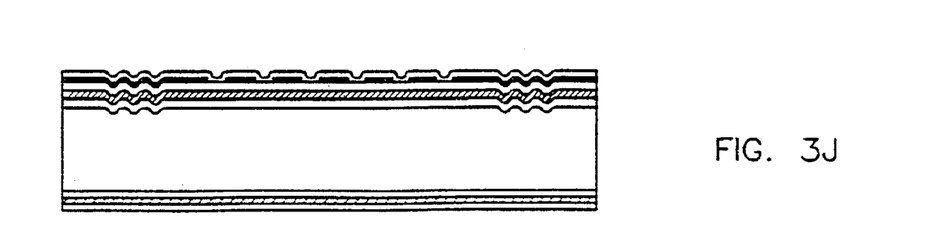
Figure 3K:
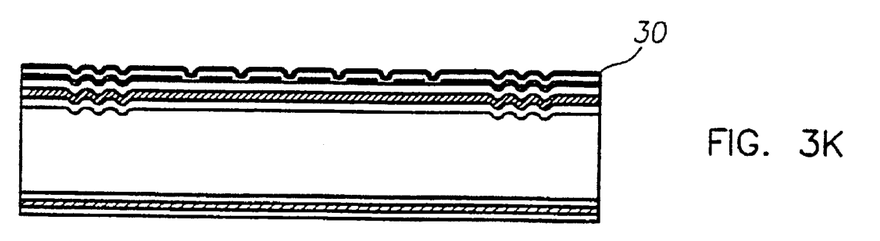
Figure 3L:
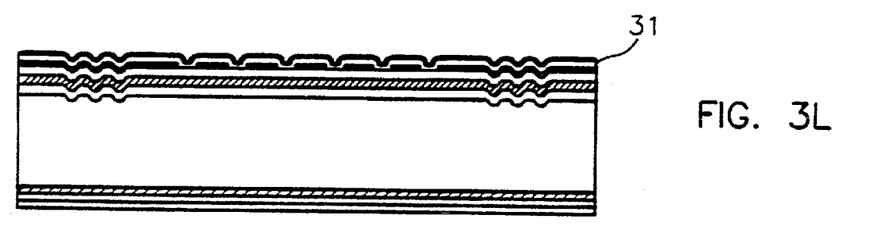
Figure 3M:
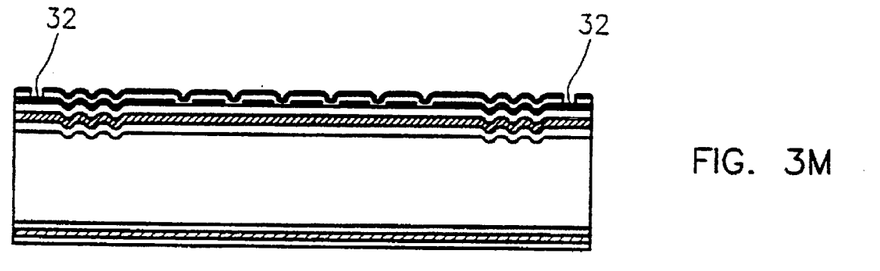
Figure 3N:
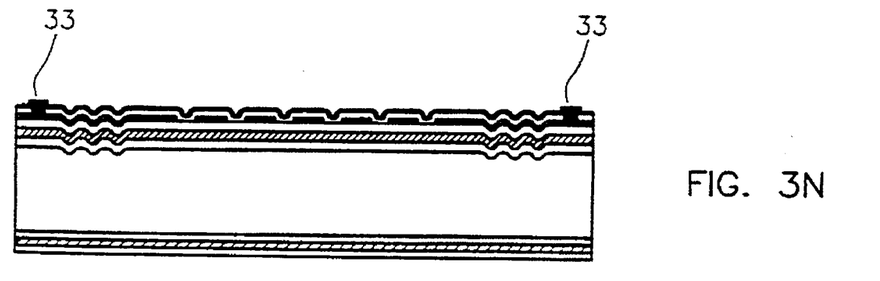
Figure 3O:
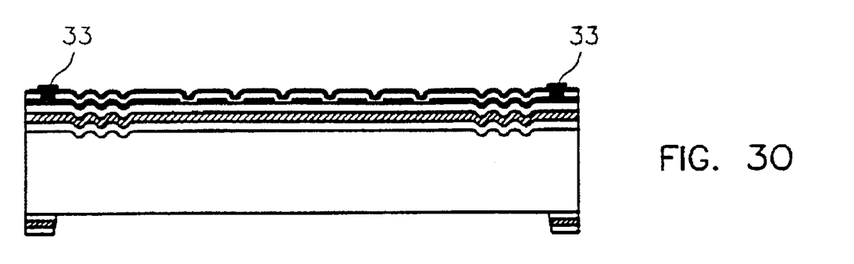
Figure 3P:
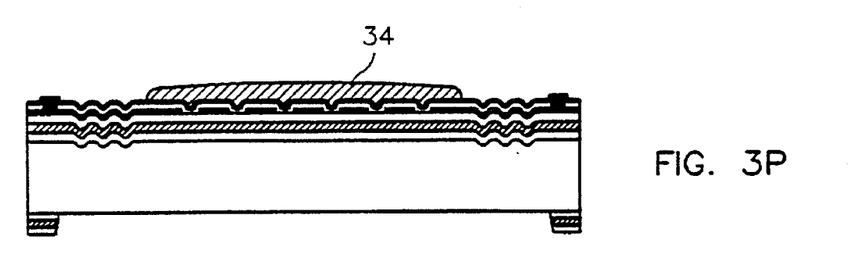
Figure 3Q:
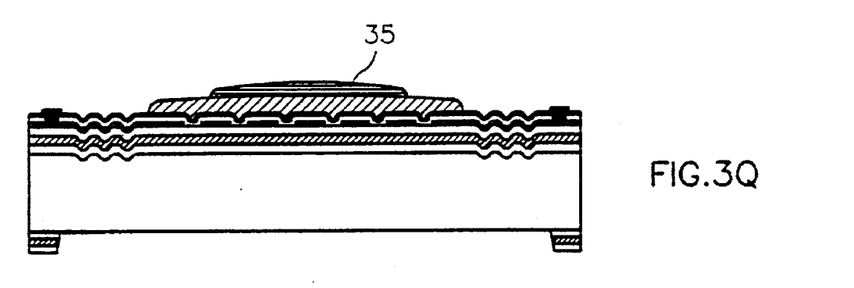
Figure 3R:
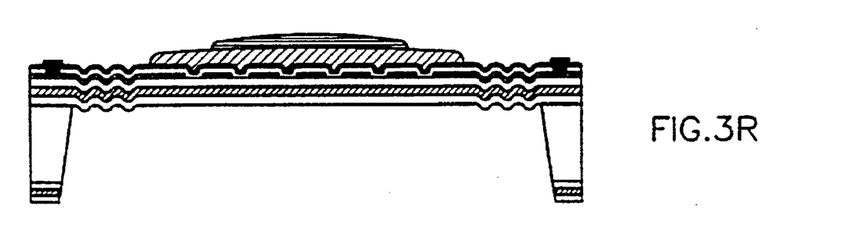

FIGS. 3A–3R are cross-sectional views of the substrate of the monolithic gas sensor fabricated in accordance with the preferred embodiment of the invention as depicted in the selected process stages. The exemplified process for the fabrication of the substrate structure may be described in the following paragraphs.

(1) In FIG. 3A, a silicon substrate having the (100) crystal direction and polished on both surfaces are utilized as the substrate for the fabrication of the sensing element. Then in FIG. 3B, one surface of the substrate is processed in a plasma etching procedure utilizing an aluminum layer as the shielding mask 24, so as to form the corrugation regions seen in FIG. 3C.

(2) The shielding mask 24 is then removed in FIG. 3D, followed by a thermal oxidation against both the top and bottom surfaces of the substrate. This forms the silicon oxide layers 25 on both surfaces as is seen in FIG. 3E.

(3) In FIG. 3F, a silicon-rich silicon nitride layer 26 is grown over both the top and bottom surfaces of the substrate.

(4) In FIG. 3G, surface of each of the top and bottom silicon-rich silicon nitride layers 26 is oxidized, so that a thin layer of silicon oxide 27 may be formed.

(5) Over the surface of the top silicon oxide layer 27, as is seen in FIG. 3H, a layer of polysilicon 29 is grown. This polysilicon layer 29 is used to form the heating resistor in the following fabrication process steps.

(6) In FIG. 3I, the polysilicon layer 29 of FIG. 3H is etched and patterned, and an oxidation procedure follows to form a polysilicon oxide layer as is shown in FIG. 3J.

(7) In FIG. 3K, the oxide layer formed in FIG. 3J is coated with a layer of aluminum 30, which is oxidized in a high temperature water vapor environment to form an aluminum oxide ceramic layer 31 shown in FIG. 3L.

(8) Contact openings 32 shown in FIG. 3M are then formed at the designated locations over the surface of the substrate. These openings 32 reach down to the polysilicon layer (29 of FIG. 3H) and can be used to form contact electrodes 33 utilizing gold as is seen in FIG. 3N.

(9) In FIG. 3O, center portion of the oxide and silicon-rich silicon nitride layers over the bottom surface of the substrate are removed, forming an exposed window allowing for the subsequent etching in the substrate.

(10) Two subsequent screen printing procedures are then performed in FIG. 3P to form a layer of tin-oxide-based material 34 on top of the aluminum oxide layer first, and then a catalyst layer 35 is formed over the surface of the tin-oxide-based sensor layer 34 in the second screen printing procedure as is seen in FIG. 3Q.

(11) Finally, in FIG. 3R, a wet anisotropic etching procedure is then implemented to remove a large portion of the substrate, resulting in the inventive configuration as shown in the drawing. In the process of the anisotropic etching, a protective mask layer may be formed over the surface of the top surface of the device substrate at this stage so as the protect the sensor film formed over the top surface from being inadvertently contaminated or damaged in the etching procedure.

Figure 4:
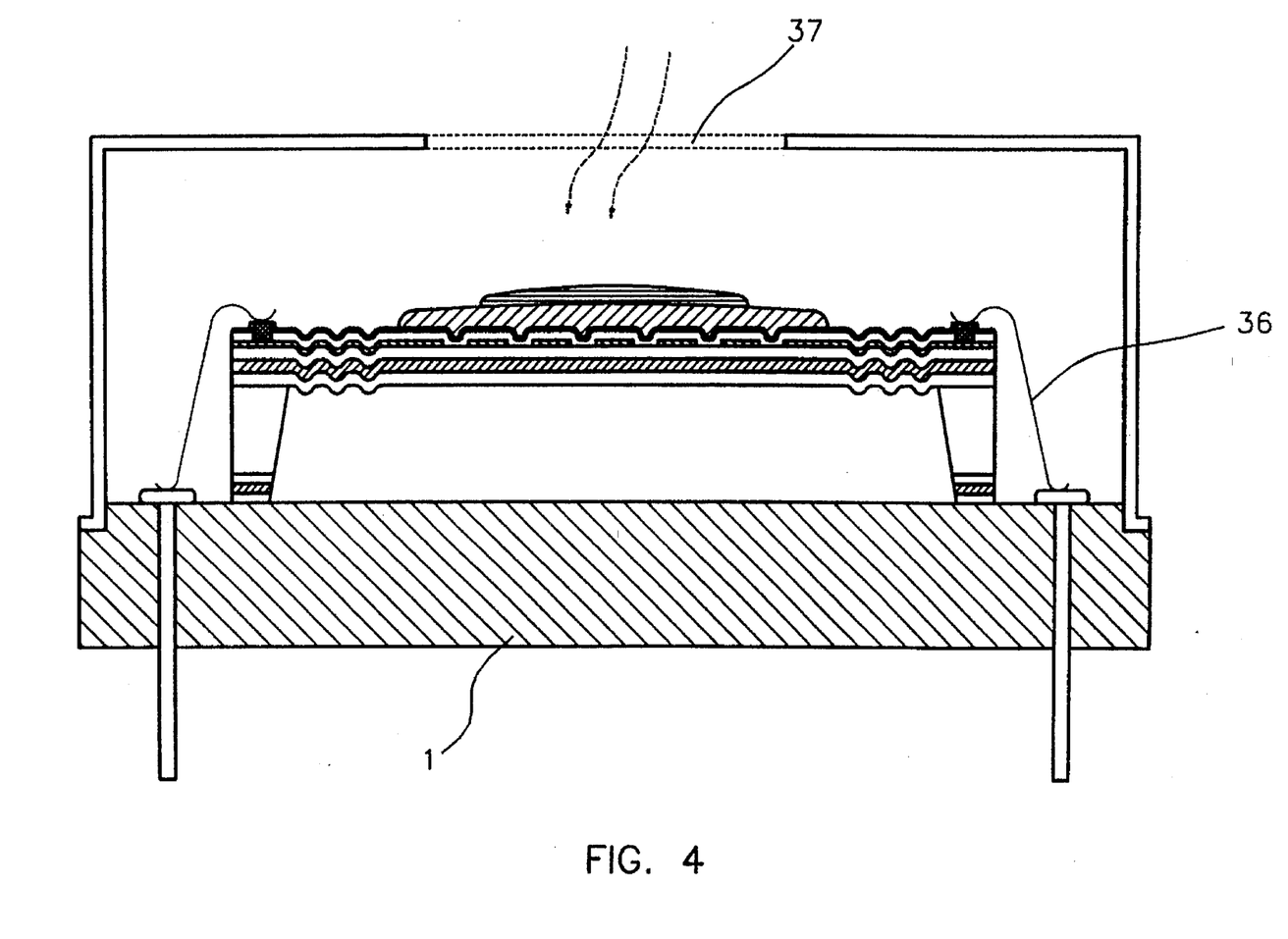
FIG. 4 shows the cross-sectional view of the monolithic gas sensor of the invention as is sealed in a device carrier.

FIG. 4 shows the cross-sectional view of the monolithic gas sensor of the invention as is sealed in a device carrier. The sensing element is carrier over the surface of a supporting base 1 and connected electrically to the lead frame of the sensing element via gold bonding wires 36. The space above the sensor film inside the device protective casing allows for free entrance of external air via the gas entrance 37 formed in the sensing element protective casing.

In the procedural steps outlined in FIGS. 3A–3R, front-side anisotropic etching procedures are employed to fabricate the substrate structure for the single-chip sensing element of the invention. Back-side anisotropic etching procedures may, however, also be employed, for example, to form the suspended substrate structure.

As such, the single-chip sensing element featuring the substrate structure fabricated as described in the procedural steps of the above preferred embodiment may feature improved resistance against thermal stress. Moreover, power consumption characteristics is also improved by significant reduction in thermal loss. Further, the substrate structure of the single-chip sensing element of the invention may still be compatible to the conventional techniques of making sensing elements utilizing tin-oxide-based material.

Thus, as persons skilled in the art may well appreciate, the above description of the preferred embodiment of the invention is intended only for the purpose of description, not for the limitation to the scope of the invention. Modifications to the outlined embodiment of the invention may be apparent and should be considered to be within the scope of the invention as recited in the claims which follow.

What is claimed is:

1. A substrate structure of monolithic gas sensor used for a single-chip sensing element, said substrate structure being formed as a thermal resistant and insulating suspended thin plate configuration on a single crystal silicon substrate, wherein said thin plate having formed thereon a heating resistor and coated with tin-oxide-based reducing gas-sensitive material, wherein said thermal resistant thin plate formed on the silicon substrate comprises a native silicon oxide layer, a silicon-rich silicon nitride layer deposited on said native silicon oxide layer, and a top silicon oxide layer formed by thermal oxidation of a surface layer of said deposited silicon-rich silicon nitride layer, thereby forming an oxide-nitride-oxide sandwiched design of composite configuration relieving mechanical stresses internal to said thin plate;

said suspended thermal resistant thin plate has corrugation portions formed near the plate edges for relieving mechanical stresses arising from thermal expansion of said silicon substrate and said thin plate when heated to high temperature; and said heating resistor formed on said thin plate comprises a polysilicon layer and is covered first by a passivation layer and then by an aluminum oxide layer having a thickness of about several hundred angstroms; and said coated tin-oxide-based material is formed by thick-film screen printing to form a sensor film for said single-chip sensing element.

2. The substrate structure of claim 1, wherein said aluminum oxide layer over said heating resistor is formed by a physical vapor deposition procedure of aluminum oxide material and directly deposited over the surface of said passivation layer.

3. The substrate structure of claim 1, wherein said aluminum oxide layer over said heating resistor is formed by depositing aluminum over the surface of said passivation layer and then causing said passivation layer to undergo chemical oxidation where said passivation layer becomes oxidized in a water vapor environment heated to a temperature over about 450° C.

4. The substrate structure of claim 1, wherein said aluminum oxide layer over said heating resistor is formed by depositing aluminum over the surface of said passivation layer to form an Aluminum-coated boundary layer conducting galvanic operations that make said boundary layer become electrochemically oxidized into an anodic oxide layer.

5. The substrate structure of claim 1, wherein said heating resistor comprises polysilicon material and said passivation layer comprises polysilicon oxide obtained by thermal oxidation of the surface layer of said heating resistor polysilicon material.

* * * * *